(12) United States Patent
Hervy (10) Patent No.: US 10,105,256 B2
(45) Date of Patent: Oct. 23, 2018

(54) INTRAORAL FUNCTIONAL DEVICE FOR RELIEVING OBSTRUCTIVE SLEEP APNEA SYNDROM, SNORING AND/OR OTHER AIRWAY DISORDERS

(71) Applicant: Michele Hervy, Noisy-le-Sec (FR)

(72) Inventor: Michele Hervy, Noisy-le-Sec (FR)

( * ) Notice: Subject to any disclaimer, the term of this patent is extended or adjusted under 35 U.S.C. 154(b) by 255 days.

(21) Appl. No.: 14/420,499

(22) PCT Filed: Aug. 9, 2013

(86) PCT No.: PCT/EP2013/066705
§ 371 (c)(1),
(2) Date: Feb. 9, 2015

(87) PCT Pub. No.: WO2014/023824
PCT Pub. Date: Feb. 13, 2014

(65) Prior Publication Data
US 2015/0223968 A1    Aug. 13, 2015

(30) Foreign Application Priority Data
Aug. 10, 2012 (EP) ..................... 12180022

(51) Int. Cl.
*A61F 5/56* (2006.01)
(52) U.S. Cl.
CPC ................ *A61F 5/566* (2013.01); *A61F 5/56* (2013.01)
(58) Field of Classification Search
CPC .......... A61F 5/56; A61F 5/566; A61F 5/0006; A61F 5/003; A61F 2005/563;
(Continued)

(56) References Cited

U.S. PATENT DOCUMENTS 3,224,442 A * 12/1965 Stubbs ..................... A61B 1/24
128/859
3,556,093 A * 1/1971 Quick ....................... A61F 5/58
433/6

(Continued)

FOREIGN PATENT DOCUMENTS

EP    0 679 378 A1    11/1995
EP    2 181 678 A1    5/2010
(Continued)

OTHER PUBLICATIONS

McKeen, Laurence W. (2014) Plastics Used in Medical Devices. Handbook of Polymer Applications in Medicine and Medical Devices.*
(Continued)

*Primary Examiner* — Keri J Nelson
*Assistant Examiner* — Adam Baker
(74) *Attorney, Agent, or Firm* — Young & Thompson (57) ABSTRACT

An intraoral device (1) includes upper cooperating elements (2) adapted to cooperate with the upper jaw (4) and lower cooperating elements (3) adapted to cooperate with the lower jaw (5); a bracket (19) fixed in the cooperating elements (2,3), the bracket (19) supports a target (18) aiming at inducing mandibular advancement and attracting the tip of the tongue; the target (18) being centered, in a transverse plane, with regard to the cooperating elements (2,3). The device (1) further includes stimulating elements (17) for stimulation of the tongue muscles, preferably the genioglossus, involving reflex exploration of the stimulating elements (17) by the tongue. The device (1) may be used for relieving obstructive sleep apnea syndrome, snoring and/or other airway disorders.

18 Claims, 6 Drawing Sheets

(58) Field of Classification Search
CPC . A61M 16/049; A61M 16/0495; A61B 13/00; A63B 23/023; A63B 71/085; A63B 71/086; A63B 71/088; A62B 9/06; B29L 2031/7412; A61J 17/02; A61J 17/001; A61J 17/00; A61J 17/006; A61H 2015/0014; A61C 7/00
USPC ............ 128/848, 860; 602/902; 601/15, 19; 606/234, 235; 433/6, 7, 22
See application file for complete search history.

(56) References Cited

U.S. PATENT DOCUMENTS

| | | | | |
|---|---|---|---|---|
| 3,818,906 A * | 6/1974 | Stubbs | ...................... | A61B 1/24 |
| | | | | 128/860 |
| 4,637,796 A * | 1/1987 | Korn | ........................ | A61C 7/00 |
| | | | | 433/7 |
| 5,092,346 A | 3/1992 | Hays et al. | | |
| 5,624,257 A * | 4/1997 | Farrell | ...................... | A61C 7/08 |
| | | | | 128/861 |
| 5,947,724 A * | 9/1999 | Frantz | ...................... | A61F 5/566 |
| | | | | 128/848 |
| 6,082,996 A * | 7/2000 | Haskell | .................... | A61C 7/00 |
| | | | | 433/18 |
| 6,126,678 A * | 10/2000 | Aaltonen | ............... | A61C 19/06 |
| | | | | 604/77 |
| 6,164,278 A | 12/2000 | Nissani | | |
| 6,237,601 B1 * | 5/2001 | Kittelsen | ................. | A61F 5/566 |
| | | | | 128/859 |
| 7,857,831 B2 * | 12/2010 | Ishikawa | ................ | A63B 23/18 |
| | | | | 128/861 |
| 2007/0079833 A1 | 4/2007 | Lamberg | | |
| 2008/0190437 A1 | 8/2008 | Hervy-Auboiron | | |
| 2009/0178684 A1 | 7/2009 | Greenburg | | |
| 2010/0184566 A1 | 7/2010 | Munehiro | | |
| 2011/0214678 A1 * | 9/2011 | Zhang | ..................... | A61F 5/566 |
| | | | | 128/848 |
| 2011/0315149 A1 * | 12/2011 | Tielemans | .............. | A61F 5/566 |
| | | | | 128/848 |
| 2012/0145166 A1 | 6/2012 | Fallon et al. | | |

FOREIGN PATENT DOCUMENTS

| | | |
|---|---|---|
| WO | 2007-141640 | 12/2007 |
| WO | 2009/096889 A1 | 8/2009 |
| WO | 2011/060103 A1 | 5/2011 |

OTHER PUBLICATIONS

Willerth SM, Sakiyama-Elbert SE (2007) Approaches to neural tissue engineering using scaffolds for drug delivery. Adv Drug Deliv Rev 59:325-338.*
European Search Report, dated Dec. 13, 2012, from corresponding EP application (EP 1218022).
International Search Report, dated Dec. 6, 2013, from corresponding PCT application.

* cited by examiner

INTRAORAL FUNCTIONAL DEVICE FOR RELIEVING OBSTRUCTIVE SLEEP APNEA SYNDROM, SNORING AND/OR OTHER AIRWAY DISORDERS

FIELD OF INVENTION

The present invention relates to an intraoral functional device for relieving obstructive sleep apnea syndrome, snoring and/or other airway disorders. Especially, the device of the present invention comprises upper cooperating means adapted to cooperate with the upper jaw and lower cooperating means adapted to cooperate with the lower jaw, characterized in that the device comprises a bracket fixed in the cooperating means, said bracket supports a target aiming at attracting the tip of the tongue; said target being centered, in a transverse plane, with regard to the cooperating means.

BACKGROUND OF INVENTION

The sleep apnea (or sleep apnoea) syndrome is a sleep disorder involving abnormal pauses in breathing or abnormally low breathing during sleep. Pauses in breathing are called apnea and abnormally low breathing is called hypopnea.

Apnea is generally defined as a cessation of air flow lasting for 10 seconds or more and may occur 5 to 30 times or more per hour. Hypopnea is generally defined as a reduction in air flow of at least 50% for at least 10 seconds.

Three types of sleep apnea are described: central (CSA), obstructive (OSA) and mixed (combination of central and obstructive) sleep apnea. In CSA, breathing is disrupted by a lack of neurological control of the respiratory effort; in OSA, by a physical upper airway obstruction despite to respiratory effort.

It is estimated that the sleep apnea syndrome, and particularly obstructive sleep apnea, afflicts an estimated 2-5% of the general population. Adults but also babies and children may be affected by sleep apnea. Sleep apnea is more common in men than in women.

Sleep apnea may be diagnosed by an overnight sleep test called polysomnogram (PSG). This test enables determining indexes reflecting the severity of the disease: Apnea Hypopnea Index (AHI) and Respiratory Disturbance Index (RDI). The AHI corresponds to the quantity of apneic events per hour of sleep. Above 5 for AHI, the patient is considered as suffering from sleep apnea, and the severity may be quantified.

The disease is quantified in terms of respiratory disturbance per hour. Mild disease begins at 2-3 apneas per hour and in the more severe cases, it may raise up to one hundred or more per hour.

Another test for assessing sleep apnea is oximetry. This test may be performed at patient's home. Oximetry aims at monitoring saturation of hemoglobin and is a very sensitive method.

People suffering from sleep apnea undergo sleep fragmentation and intermittent, complete or nearly complete, cessation of ventilation during sleep with potentially severe degrees of oxyhemoglobin unsaturation. Symptoms associated with sleep apnea are daytime sleepiness, slower reaction time, cognitive dysfunction, cardiac dysrhythmia, pulmonary-artery hypertension, congestive heart failure. Hypersomnolent sleep apnea patients may be at risk for excessive mortality from these factors as well as an elevated risk for accidents when driving or operating other potentially dangerous equipment.

While sleeping, a normal individual is "at rest", breathing is regular and oxygen levels stay fairly constant. Any sudden drop in oxygen or excess of carbon dioxide strongly stimulates the brain's respiratory centers to breath.

In central sleep apnea, the brain's respiratory control centers are imbalanced during sleep. In CSA patients, basic neurological controls for breathing fail to give the signal to inhale, causing the individual to miss one or more cycles of breathing and leading to a drop of oxygen level and an increase of carbon dioxide level.

It is generally admitted that the mechanism of obstructive sleep apnea syndrome involves anatomic or functional abnormalities of the upper airway which result in increased air flow resistance. These abnormalities may include narrowing the upper airway due to suction forces developed during inspiration, the effect of gravity pulling the tongue back to the pharyngeal wall and/or insufficient muscle tone in the upper airway dilator muscles, especially the genioglossus. In apneic patients, the latency time of implementation of the genioglossus is elongated. Moreover, in the case of obese patients, the presence of excessive soft tissues in the anterior and lateral neck applies pressure on internal structures and narrows the airway.

It is admitted that the main reason for snoring and obstructive sleep apnea is the relaxation of the tongue and pharyngeal walls. In awaken patients, these tissues have normal air tone and air passes in and out of the lungs during respiration. During sleep of apneic or snoring patients, the musculature retaining these tissues relaxes. When air is inspired, the tongue and the posterior walls of the pharynx collapse, causing snoring or partial or complete obstruction of the airway.

The lack of respiration implies inadequate blood oxygenation (hypoxia) and raises the carbon dioxide levels (hypercadmia). Hypoxia induces diverse effects on the body, especially increase of the heart rate or cyanosis. At worst, death may occur. However, in general, the oxygen desaturation that occurs induces a transition to a lighter sleep stage, usually without wakefulness. This transition brings a return to tonicity of the muscles of the upper airway, allowing normal breathing. The person then return to a deeper sleep stage and the process is repeated.

This fragmentation of the sleep induces a poor quality of the sleep, resulting in persons feeling tired and falling asleep at inappropriate time during the day and to other symptoms described above.

Moreover, some studies have shown that hypoxia promotes angiogenesis which increases vascular and tumor growth and higher incidence of cancer mortality.

A first action to limit sleep apnea and especially obstructive sleep apnea comprises lifestyle changes, such as avoiding alcohol or muscle relaxants, losing weight, quitting smoking. Patients may also sleep at a 30-degree elevation of the upper body or in a lateral position.

The most widely used treatment of obstructive sleep apnea is continuous positive airway pressure (CPAP) to maintain the airway of the patient in a continuously open state during sleep. The patient typically wears a facial mask connected to a CPAP machine which generates required air pressure. The method has been found very effective but suffers from some limitations, especially because a significant proportion of sleep apnea patients do not tolerate CPAP.

Another treatment of obstructive sleep apnea implies surgical procedures. Different methods were proposed, for example nasal surgery, surgery of soft tissues or bone surgery, however, failures were reported. The poor success of these interventions, combined with high morbidity from some of these surgical interventions is not in favor of a surgical treatment of sleep apnea.

Pharmacological treatments were also proposed to stimulate the upper airway muscle to reduce apnea or to lower blood pH to encourage respiration, such as with acetozamide. However, until now, disappointing results were obtained and side effects were reported.

Other non-chirurgical treatments were proposed to treat obstructive sleep apnea, especially using oral devices and appliances. These treatments are based on the fact that people suffering from sleep apnea often present an important anatomical change during sleep. Especially, a change in the soft tissues such as tongue, soft palate, pharyngeal walls and/or palatine tonsils is often observed. These modifications also affect craniofacial skeleton.

It was also observed that anatomical abnormalities favor sleep apnea, such as for example craniomaxillofacial abnormalities or retrognathims, for example the position of the jaw.

Some appliances work to mechanically retain the tongue, preventing it from falling backwards or helping to reduce the collapse of the soft palate such as in EP2181678 or in US2012/145166. Patent application US2012/0145166 discloses an intra-oral mandibular advancement appliance comprising a tongue rest designed for preventing the patient's tongue from falling, under the influence of gravity, towards his throat during sleep.

Some devices were also described which actively pull on the tongue to keep it forward during sleep, such as in WO2011/060103, in WO2009/096889 and in EP0679378. European patent application EP0679378 discloses a device for preventing snoring comprising a stirrup and a tongue component movably mounted on the end of the stirrup. The stirrup is loaded by means of a spring such that the tongue component can press the tongue away from the rear soft palate while allowing swallowing.

Devices were also proposed which actively push the lower jaw forward, thereby pulling the tongue slightly forward such as in US2009/178684 and in US2007/079833.

These devices are intended to prevent the patient from exerting muscle forces on soft tissues of upper airways. However, these intraoral devices do not provided significant improvements in sleep apnea, except in mild to moderate cases.

Moreover, most of the devices of the prior art are associated with movements of teeth over time or with problems with the mandibular joint and mandibular muscles. Such side effects are related with the fact that the muscle involvement in the mandible or tongue advancement is forced, not induced. This kind of device is called active device or orthopaedic device. By "active device", it is meant a device that employs external forces to induce anatomical changes. Active devices should be understood by contrast with functional devices. By "functional device", it is meant a device that achieve anatomical changes—in the present invention, more particularly changes in the position of the jaw, the tongue and/or or the pharyngeal walls—by using the body's own natural forces. Functional devices change the functional patterns of the muscular system by causing the muscle to work.

Beyond obstructive sleep apnea, snoring and other airway disorders are also caused by a wrong position of the tongue and/or a relaxation of pharyngeal walls. Other airway disorders may be for example linked to breathing through the mouth.

There is thus a need for new intraoral appliances that enable relieving obstructive sleep apnea syndrome, snoring and/or other airway disorders, that overcome above mentioned issues and that are well tolerated by patients. Especially, the device of the present invention presents the advantage of being easy to use, not expensive, easily adaptable, easy to manufacture and not inducing side effects usually associated with prior art devices. The device of the invention is a functional device.

In patent application US2008/190437, the Applicant proposed a first functional device inducing reflex mandibular advancement. The device of US2008/190437 comprises means for exerting pressure on the mucous zone covering the mental spines of the lower jaw. The pressure on the mucous zone covering the mental spines induces a reflex mandibular advancement resulting in the opening of upper airways. As mandibular advancement is induced and not forced, the functional device of US2008/190437 does not lead to movements of teeth overtime and to problems with the mandibular joint and mandibular muscles. Results obtained on patient with this device were very encouraging and the Applicant continued searching to provide even more efficient device.

The tongue is mainly made of muscles. Especially, the tongue comprises four extrinsic muscles (genioglossus, hyoglossus, styloglossus and palatoglossus) which originate from bone and extend to the tongue. The main function of these extrinsic muscles is moving the tongue, enabling protrusion, retraction and side-to-side movement.

Especially, the genioglossus enables protrusion of the tongue. The genioglossus muscle is also the only pharyngeal dilator muscle. As a consequence, a stimulation of the genioglossus may induce a dilatation of the pharynx, opening upper airways.

Tongue is an explorative element, especially the tip of the tongue. When a foreign body is present into the mouth of an individual, the tongue explores it, without conscious control from the individual. During the exploration, extrinsic muscles of the tongue are solicited, especially the genioglossus and an induced movement of the jaw occurs at the same time. The movement of the jaw and the advancement of the tongue during exploration lead, among other effects, to the opening of the upper airway.

Therefore, the Applicant carried out an extensive research relative to the placement of a foreign body into the mouth of a patient afflicted by sleep apnea syndrome, snoring and/or other airway disorders to induce reflex exploration of the tongue and leading to tongue and jaw advancement and consequently to airway opening. In other words, the device of the invention intends using the sensitive propensity of the tongue to induce tongue movement.

According to the Applicant's understanding, the tongue reiterates or not its reflex exploration of the foreign body depending of its shape and of its ability to move.

The Applicant showed that a ball-shaped element was particularly appreciated by the tongue for exploration, even more if the ball-shaped element is movable.

The present invention thus relates to a novel intraoral device comprising upper cooperating means adapted to cooperate with the upper jaw and lower cooperating means adapted to cooperate with the lower jaw, characterized in that the device comprises a bracket fixed in the cooperating means, said bracket supports a target aiming at attracting the tip of the tongue; said target being centered, in a transverse plane, with regard to the cooperating means.

In one embodiment, stimulating means for stimulation of the tongue muscles, preferably the genioglossus, involving reflex exploration of said means by the tongue comprise a target able to rotate on itself. In a preferred embodiment, the target is carried by a bracket. In a preferred embodiment, the target is ball-shaped.

In the device of the invention, means for stimulation of the tongue muscles, preferably the genioglossus, are also able to exert pressure on the mucous zone covering the mental spines of the lower jaw. Therefore, but without willing to be bound by a theory, it is the Applicant understanding that the device of the present invention both promotes:

a reflex mandibular advancement by pressure on the mucous zone covering the mental spines of the lower jaw; and a reflex exploration by the tongue leading to genioglossus stimulation and tongue advancement.

According to the Applicant's understanding the following occur when a user bears the device of the invention:

During apnea, the lower jaw moves backward. In patients bearing the device of the invention, when the lower jaw moves backward, it encounters the target. The target exerts a pressure on the mucous zone covering the mental spines of the lower jaw. As explained above, a reflex mandibular advancement occurs in response to pressure. It is though that the tongue then explores the mouth in order discover the origin of the pressure. When the tongue explores the target, the genioglossus is stimulated. The stimulation of the genioglossus has at least two effects:

it induces the dilatation of the pharynx, opening upper airways; and it muscles the genioglossus.

The invention thus relates to a device for inducing reflex exploration by the tongue and reflex mandibular advancement leading to induced tongue and jaw advancement. The device of the invention thus induces airways opening and may be used in the treatment, prevention and/or correction of obstructive sleep apnea syndrome, snoring and/or other airway disorders.

The use of the functional device of the invention is intended to strengthen the genioglossus so that it retrieves sufficient muscle tone in order to induce correct dilatation of the pharynx. The stimulation of the genioglossus obtained by using the device of the invention is expected to lead to a correction of airway disorders, especially of obstructive sleep apnea syndrome. In one embodiment, using the device of the invention enables a reeducation of the genioglossus.

REFERENCES

1 Device
2 Upper cooperating means
3 Lower cooperating means
4 Upper jaw
5 Lower jaw
6 Tray
7 Fixing means
8 Hooks/Clasp (preferentially Adam's clasp)
9 a, b, c, d Pairs of incisors
10 a, b Pair of canines
11 a, b, c, d Pairs of premolars
12 a, b Pair of Molars
13 Means of fixation with the aid of at least one premolar
14 Means of fixation with to at least one molar
15 Arm (preferentially Ball end clasp)
16 Breathing hole
17 Stimulating means
18 Target
19 Bracket
20 Centering means
21 Front end of the device
22 Internal slope of the lower cooperating means

DETAILED DESCRIPTION

The present invention is now described on the basis of FIGS. 1 to 6, which do not in any way limit the scope of the present invention.

Throughout the description the same elements are designated by the same reference numbers.

The present invention relates to a device to be inserted in the mouth of an animal, preferably a human, said mouth having an upper and a lower jaw, the device comprising:

upper cooperating means (2) adapted to cooperate with the upper jaw;

lower cooperating means (3) adapted to cooperate with the lower jaw;

a bracket (19) fixed in the cooperating means (2, 3) and supporting a target (18), characterized in that said target (18) attracts the tongue, preferably the tip or the apex of the tongue, and induces mandibular advancement.

In one embodiment, said target (18) is located in the inferior extension of the lower cooperating means (3).

In one embodiment, said target (18) is located from 0.1 to 30 millimeters behind the front end (21) of the device (1).

In one embodiment, said target (18) is centered, in a transverse plane, with regard to the cooperating means (2, 3).

In one embodiment, said target (18)

is located in the inferior extension of the lower cooperating means (3);

is located from 0.1 to 30 millimeters behind the front end (21) of the device (1); and is centered, in a transverse plane, with regard to the cooperating means (2, 3).

In one embodiment, said target (18) is a stimulating means (17) attracting the tongue, preferably the tip of the tongue, inducing mobilization of the protractor muscles of the tongue, and inducing reflex mandibular advancement; said mandibular advancement being held by muscles, preferably being held only by muscles.

In one embodiment, said stimulating means (17) induces reflex mandibular advancement.

In one embodiment, said stimulating means (17) stimulates the tongue muscles, preferably the protractor tongue muscles, more preferably the genioglossus, and involves reflex exploration by the tongue of said stimulating means (17).

In one embodiment, said upper and lower cooperating means (2) and (3) are fixed one relative to the other.

In one embodiment, said upper cooperating means (2) comprises fixing means (7) to the upper jaw; said fixing means comprise at least one clasp, preferably an Adam's clasp or a ball end clasp.

In one embodiment, said target (18) is a moving target, preferably a rotating target.

In one embodiment, said bracket (19) has an overall U-shape, the extremities of the two arms of the U being embedded in the cooperating means (2, 3) and wherein the target (18) is on the lower part of the U.

In one embodiment, said bracket (19) comprises centering means (20) for centering target (18) relative to the device (1).

In one embodiment, said target (18), said upper cooperating means (2) and/or said lower cooperating means (3) are made of a biocompatible, non-allergenic substance, preferably a polymer or a resin.

In one embodiment, said target (18) is spherical, spheroidal or ellipsoidal and is able to rotate around at least one axis, preferably on itself around one axis of revolution.

In one embodiment, said target (18) comprises a metallic tube through which pass the bracket (19), preferably a metallic bracket (19).

In one embodiment, said target (18) comprises an active agent.

In one embodiment, the present invention relates to said device (1) for treating, preventing and/or correcting obstructive sleep apnea syndrome, snoring and/or other airway disorders in a subject in need thereof.

In one embodiment, the present invention relates to said device (1) for treating, preventing and/or correcting obstructive sleep apnea syndrome, snoring and/or other airway disorders in a subject in need thereof, wherein said subject is a child.

In one other embodiment, the present invention also relates to a device to be inserted in the mouth of an animal, preferably a human, said mouth having an upper and a lower jaw, the device comprising:
  upper cooperating means (2) adapted to cooperate with the upper jaw;
  lower cooperating means (3) adapted to cooperate with the lower jaw, characterized in that the device comprises stimulating means (17) for stimulation of the tongue muscles, preferably the genioglossus involving reflex exploration of said stimulating means (17) by the tongue.

In another embodiment, the present invention also relates to a device to be inserted in the mouth of an animal, preferably a human, said mouth having an upper and a lower jaw, the device comprising:
  upper cooperating means (2) adapted to cooperate with the upper jaw;
  lower cooperating means (3) adapted to cooperate with the lower jaw;
  a bracket (19) fixed in the cooperating means (2, 3) and supporting a target (18),
  characterized in that said target (18) ensures induces mobilization of the protractor muscles of the tongue and reflex mandibular advancement.

In another embodiment, the present invention also relates to a device to be inserted in the mouth of an animal, preferably a human, said mouth having an upper and a lower jaw, the device comprising:
  upper cooperating means (2) adapted to cooperate with the upper jaw;
  lower cooperating means (3) adapted to cooperate with the lower jaw;
  a bracket (19) fixed in the cooperating means (2, 3) and supporting a target (18),
  characterized in that said target (18) ensures protraction of the tongue and of the mandible.

The present invention further relates to a method of manufacturing the device of the invention, the method comprising producing the device of the invention by computer-aided manufacturing.

Figure 1:
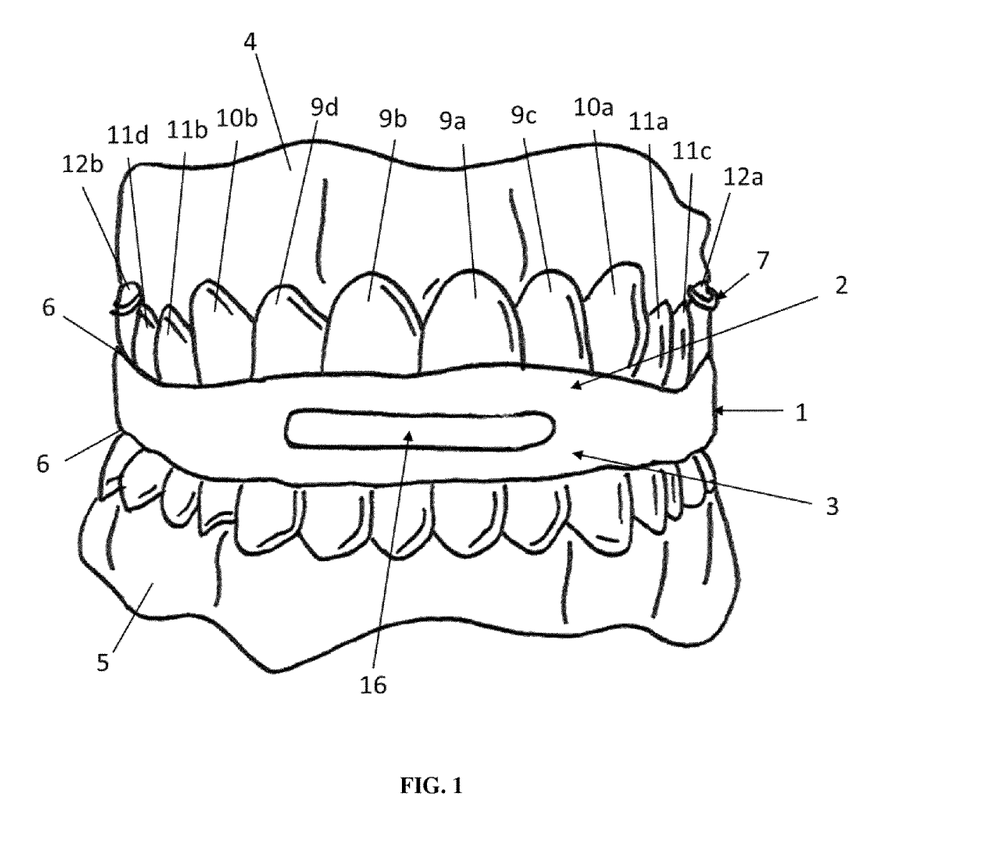
FIG. 1 is a drawing representing a front view of the device according to the invention placed in a user's mouth.

FIG. 1 shows a front view of the device according to the invention placed in a user's mouth.

According to one embodiment, the device (1) according to the invention has upper cooperating means (2) and lower cooperating means (3) that are adapted to cooperate with the upper jaw (4) and lower jaw (5), respectively, of a user.

In the sense of the present invention, "cooperate" means that the upper and lower cooperating means (2) and (3) are designed to receive, respectively, the upper and lower jaws (4) and (5), in a controlled manner. The lower and upper jaws (5) and (4) may be fixed or not with respect to respectively said lower or upper cooperating means respectively (3) and (2).

In one embodiment, the upper and lower cooperating means (2) and (3) are integrally formed in one piece. In one embodiment, the upper and lower cooperating means (2) and (3) are monobloc. In one embodiment, said upper and lower cooperating means (2) and (3) are fixed one relative to the other. In one embodiment, the upper cooperating means (2) cannot slide with respect to the lower cooperating means (3), or conversely. In another embodiment of the present invention, the position of the lower jaw (5) cannot be adjusted, in use, with respect to the upper jaw (4), or conversely. In one embodiment of the present invention, the lower jaw (5) cannot move, in use, with respect to the upper jaw (4), or conversely.

In one embodiment, the lower cooperating means (3) is a ramp. In one embodiment, the lower cooperating means (3) is not a ramp but a tray (6). In one embodiment, the upper cooperating means (2) is a tray (6). In one embodiment, the upper cooperating means (2) is a tray (6), which cooperates with the upper jaw (4) along the whole dental arch. In one embodiment, the lower cooperating means (3) is a tray (6). In one embodiment, the lower cooperating means (3) is a tray (6), which cooperates with the lower jaw (5) along the whole dental arch.

In one embodiment, the lower cooperating means (3) does not comprise a triangular leaf. In one embodiment, the upper cooperating means (2) covers the lip side of the maxillary anterior teeth. In one embodiment, the upper cooperating means (2) covers the tongue side of the maxillary anterior teeth.

In one embodiment, the device (1) of the present invention does not comprise a dental plate bearing against the palate of the user. In one embodiment, the device (1) of the present invention does not comprise a palate part being in contact with a palate. In one embodiment, the device (1) of the present invention does not comprise a dorsum tongue part being in contact with a dorsum of the tongue.

In one embodiment, the device (1) of the present invention is not effective for the improvement of the teeth alignment.

In one embodiment and as shown on FIG. 1, FIG. 2, FIG. 4 and FIG. 6, the upper and lower cooperating means (2) and (3) are in the form of a tray (6) in which the teeth of the upper jaw (4) and of the lower jaw (5) are able to bear and to cooperate.

According to one embodiment, the cooperating means (2) and (3) are in the form of a tray (6) in which the totality of the teeth of the upper jaw (4) and of the lower jaw (5) are able to bear and to cooperate.

According to another embodiment, the cooperating means (2) and (3) are in the form of a tray (6) in which a part of the teeth of the upper jaw (4) and of the lower jaw (5) are able to bear and to cooperate. Preferably in this embodiment, incisors can bear in the tray (6).

According to another embodiment, the upper cooperating means (2) is in the form of a tray (6) in which the totality of the teeth of the upper jaw (4) are able to bear and to cooperate, and the lower cooperating means (3) is in the form of a tray (6) in which part of the teeth of the lower jaw (5), preferably the incisors, are able to bear and to cooperate.

According to another embodiment, the upper cooperating means (2) is in the form of a tray (6) in which the teeth of the upper jaw (4) are able to bear and to cooperate, and the lower cooperating means (3) is in the form of a ramp (6) in which part of the teeth of the lower jaw (5), preferably the incisors, are able to bear and to cooperate.

According to another embodiment, the upper and lower cooperating means (2, 3) is in the form of a tray (6) in which the teeth of the upper jaw (4) are able to bear and to cooperate, and on which the lower dental arch is impressed.

According to an embodiment, the cooperating means (2) and (3) have the general shape of a semicircle or horseshoe.

FIG. 1 shows cooperating means (2) and (3) with an open outer face, that is to say that in this embodiment when the teeth are bearing on the tray (6), the outer face of the teeth is not covered by the cooperating means (2) and (3), or is only partially covered.

According to one embodiment, cooperating means (2) and/or (3) are in the form of a tray (6) that does not cover the outer face of the teeth. According to another embodiment, cooperating means (2) and/or (3) are in the form of a tray (6) that partially covers the outer face of the teeth. According to another embodiment, cooperating means (2) and/or (3) are in the form of a tray (6) that does cover the outer face of the teeth.

Figure 4:
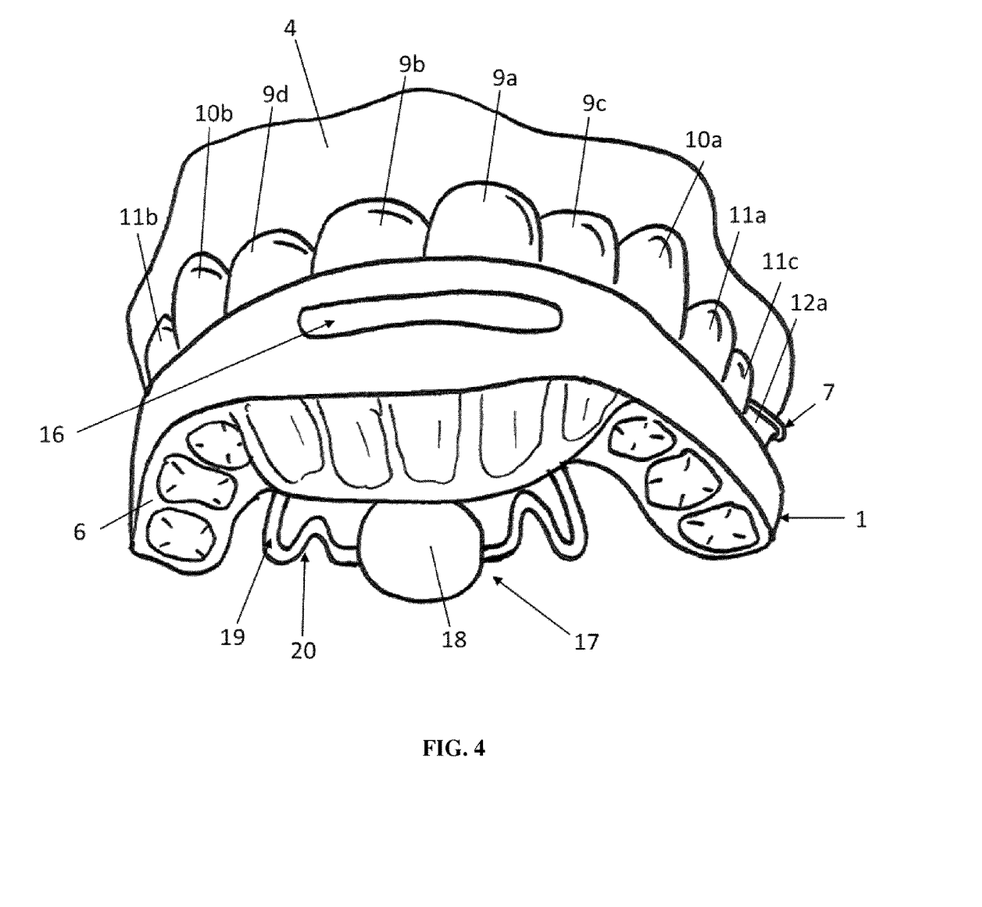
FIG. 4 is a drawing representing a perspective front view of the device according to the invention positioned on the upper jaw of a user.
Figure 5:
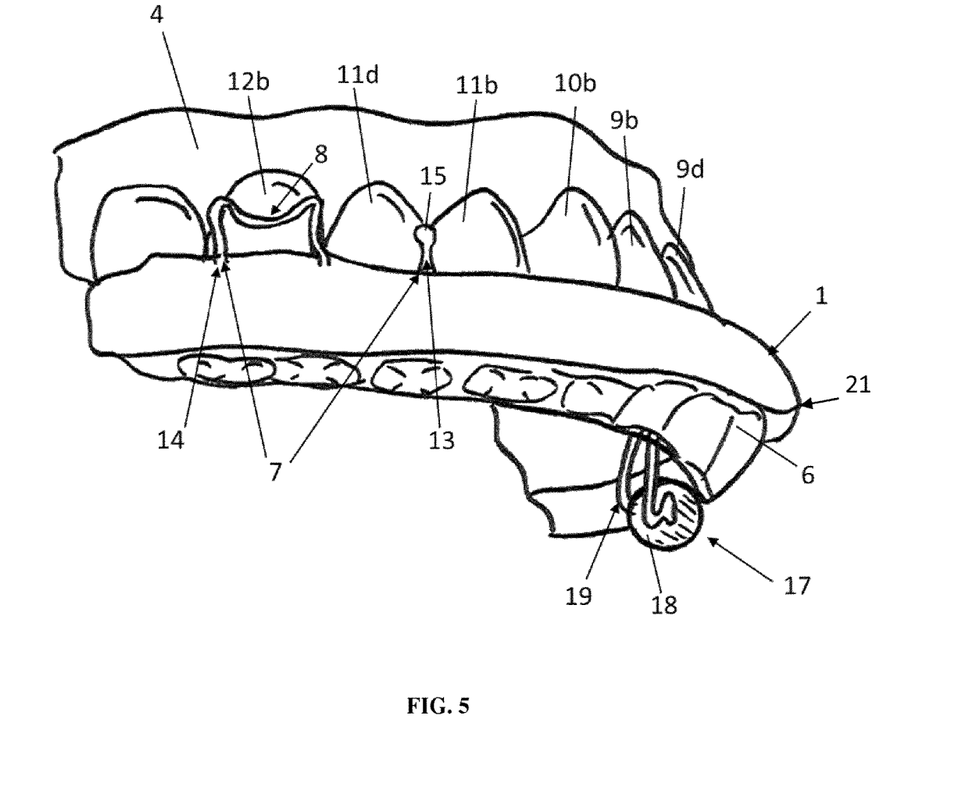
FIG. 5 is a drawing representing a perspective side view of the device according to the invention positioned on the upper jaw of a user.
Figure 6:
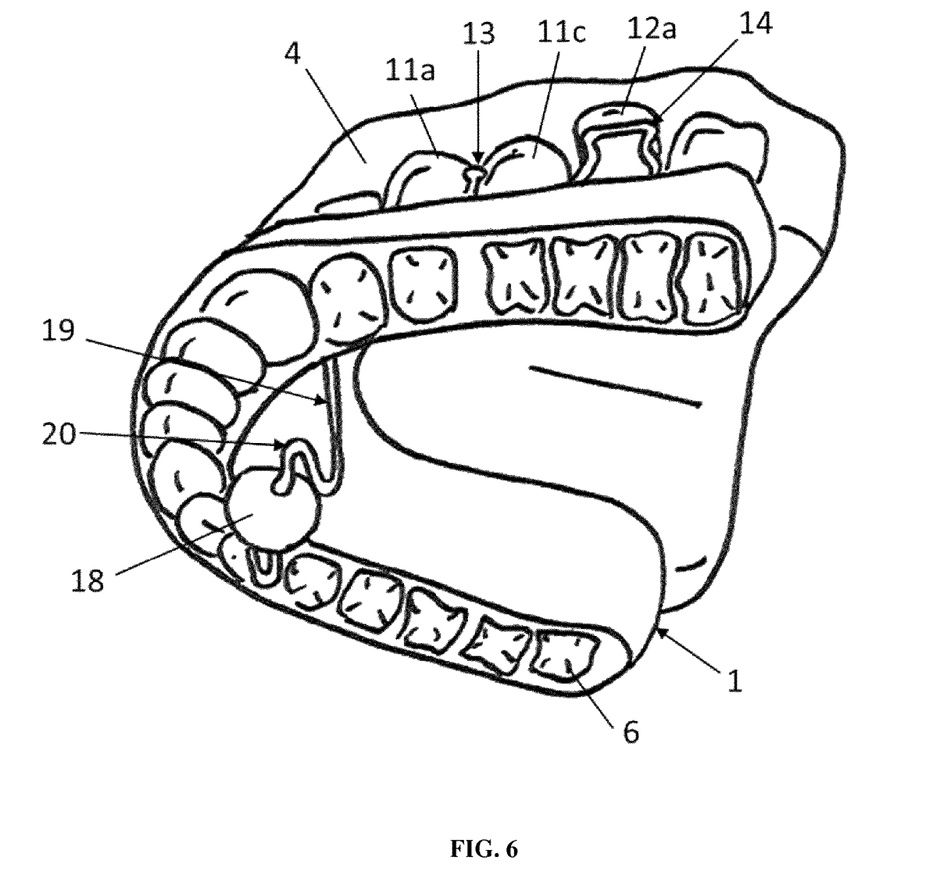
FIG. 6 is a drawing representing a perspective three-quarter view of the device according to the invention positioned on the upper jaw of a user.

According to an embodiment, and as showed in FIG. 4, FIG. 5 and FIG. 6, the upper and/or lower cooperating means (2) and/or (3) have hollows or internal cuttings of a shape matching the crowns of the teeth of the upper jaw (4) and lower jaw (5), respectively. According to an embodiment, hollows or cuttings are only present on the upper cooperating means (2) or on the lower cooperating means (3); preferably the upper cooperating means (2). According to a preferred embodiment, hollows or cuttings present on cooperating means (2) and/or (3) are formed from casts of the upper jaw (4) and lower jaw (5).

In one embodiment, the crowns of the teeth can engage totally or partially in the tray (6), thus allowing the cooperating means (2) and (3) to be held in a controlled position on the dental arches.

It is obviously within the scope of a person skilled in the art to produce such cooperating means (2) and (3).

According to an embodiment, cooperating means (2) and (3) are made of a biocompatible, non-allergenic substance, such as resin, for example acrylic resin or acetal resin, polymer or any polymer-based material know by one skilled in the art. According to another embodiment, any type of substance is conceivable for producing cooperating means (2) and (3) according to the invention, such as for instance a composite. According to one embodiment, cooperating means (2) and (3) are made of flexible resin. According to one embodiment, cooperating means (2) and (3) are made of a material which may be thermoformed to the shape of the patient's dental arches.

According to one embodiment, the device (1) on the invention comprises a breathing hole (16). The breathing hole (16) may be located between cooperating means (2) and (3) and have and an elongated shape. The breathing hole (16) allows communication between the interior and the exterior of the mouth when the use bears the device (1) of the invention. The breathing hole (16) allows an air flux to pass from the exterior of the mouth into the mouth and the contrary. The breathing hole (16) may be absent and in this case the user performs nasal breathing.

In one embodiment, the breathing hole of the present invention (16) is distinct from the target (18) or the stimulating means (17). In one embodiment, the breathing hole of the invention (16) is not designed to receive the tip of the patient's tongue. In one embodiment, the breathing hole of the present invention (16) is not designed to attract the tip of the tongue forward. In one embodiment, the target (18) of the present invention is designed to attract the tip of the tongue forward.

In one embodiment, the target (18) or the stimulating means (17) is not directly in contact with the cooperating means (2) and (3).

In one embodiment, the target (18) or the stimulating means (17) is not designed to create housing for a part of the tongue. In one embodiment, the target (18) or the stimulating means (17) is not designed to lock or trap a part of the tongue.

Figure 2:
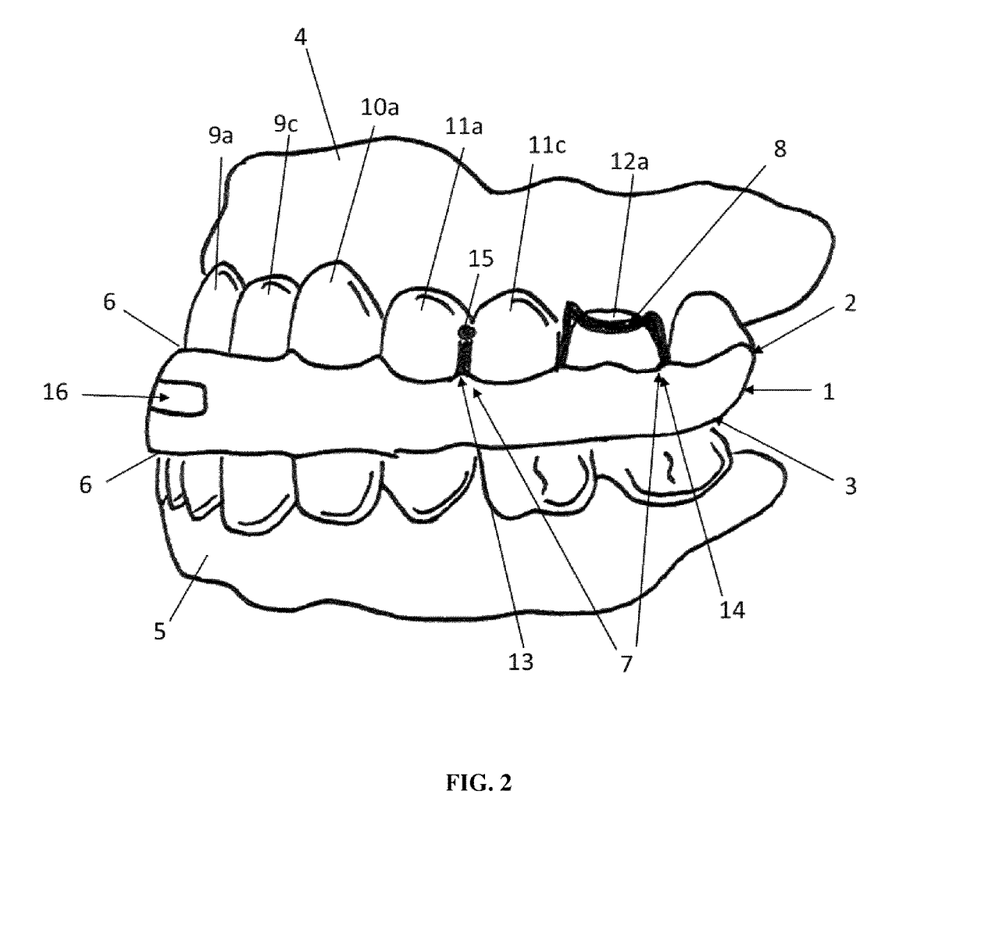
FIG. 2 is a drawing representing a side view of the device according to the invention placed in a user's mouth.

FIG. 2 shows a side view of the device according to the invention placed in a user's mouth.

According to one embodiment, fixing means (7) for fixing the device (1) on the upper jaw (4) are provided in the upper cooperating means (2). Fixing means (7) allow the device (1) to be held immovably in the user's mouth, preferably to be held immovably with respect to the upper jaw (4).

According to another embodiment, the device (1) does not comprise fixing means. In one embodiment, when the cooperating means (2) and (3) are made of flexible resin, the device (1) does not comprise fixing means. In an embodiment, the resilience of the material of the cooperating means (2) and (3) enables holding the device in the user's mouth without the need of fixing means.

In one embodiment, the fixing means (7) are in the form of hooks (8)—also named clasp-cooperating with the user's upper dental arch.

In a preferred embodiment, the fixing means (7) comprises at least one clasp, which may be any clasp that a person skilled in the art would find suitable; preferably an Adam's clasp or a ball end clasp. In said preferred embodiment, said clasp cooperates with the user's upper dental arch. In another embodiment, the fixing means (7) does not cooperate with the lower dental arch.

Each person's teeth are usually made up of two pairs of incisors (9a, 9b, 9c, 9d), one pair of canines (10a, 10b), two pairs of premolars (11a, 11b, 11c, 11d) and then molars (12a, 12b), this arrangement of the teeth applying both to the upper jaw (4) and to the lower jaw (5).

According to one embodiment, and as shown in FIG. 2, the fixing means (7) comprise means (13) of fixing with the aid of at least one premolar and means (14) of fixing to at least one molar.

In an embodiment, means (14) of fixing to at least one molar are in the form of a hook (8), presently known as an Adams hook, also called Adam's clasp.

The Adam's clasp (8) is thus advantageously produced from a hard steel wire which encloses a molar (12a) or (12b) and whose two ends are embedded in the upper cooperating means (2), preferably in the resin composition from which these cooperating means (2) are made.

It is possible for a person skilled in the art to modify the configuration of the clasp (8) depending on the molar on which it is to be fixed.

In an embodiment, means (13) for fixing the device (1) with the aid of at least one premolar are in the form of an arm (15), such as a ball end clasp, able to be inserted between the two premolars (11a) and (11c) or (11b) and (11d) of the upper jaw (4).

In a preferred embodiment, the arm (15), such as a ball end clasp, is made from an upright steel wire.

In a preferred embodiment, the device (1) comprises at least four fixing means (7) in the form of ball end clasps, preferably at least two on each side of the cooperating means (2,3), cooperating with the user's upper dental arch (i.e. with the upper jaw (4)).

In another embodiment, the device (1) comprises at least two fixing means (7) in the form of Adam's clasp, preferably at least one on each side of the cooperating means (2, 3), cooperating with the user's upper dental arch (i.e. with the upper jaw (4)).

In very preferred embodiment, the free end of the arm (15) has advantageously a bulged area of material in order not to nick or irritate the gums in the free space between the two premolars (11a) and (11c) or (11b) and (11d).

A person skilled in the art will be able to adapt the length and diameter of the arm (15) depending on the size of the premolars (11a, 11b, 11c, 11d) and of the free space between them.

In a preferred embodiment, the device (1) does not comprise fixing means (7) which cooperates with the user's lower dental arch. In said preferred embodiment, the lower jaw (5) maintains its mobility in use: during insertion of the device (1) the lower jaw (5) cooperates with the lower cooperating means (3) and the lower jaw (5) is thus located in a forward position, then the lower jaw (5), which remains free, stays in its position only due to the reflex mandibular advancement induced by the device (1) and not due to any fixation of the device (1) with respect to the lower jaw (5) such as in mandibular advancement splint of the prior art. According to said preferred embodiment, the lower jaw (5) is not fixed with respect to the lower cooperating means but the lower cooperating means offers a preferred position which is favored by the target (18) and the stimulating means (17). In said embodiment, the mandibular advancement is exclusively maintained by muscles. In said embodiment, the target (18) prevents backward movement of the lower jaw (5). The mandibular advancement is thus not forced but reflex, natural, spontaneous or induced.

In one embodiment, the device of the invention (1) is a functional device. In the sense of the present invention, a functional device achieves anatomical changes—more particularly changes in the position of the jaw, the tongue and/or or the pharyngeal walls—by using the body's own natural forces. In one embodiment, the device (1) of the invention achieves changes in the position of the jaw, the tongue and/or or the pharyngeal walls, and thus opening of the upper airways, only by muscle stimulation. In one embodiment, the device (1) is functional and not orthopaedic.

In one embodiment, the device of the invention (1) is not an active device employing external forces such as a spring.

Figure 3:
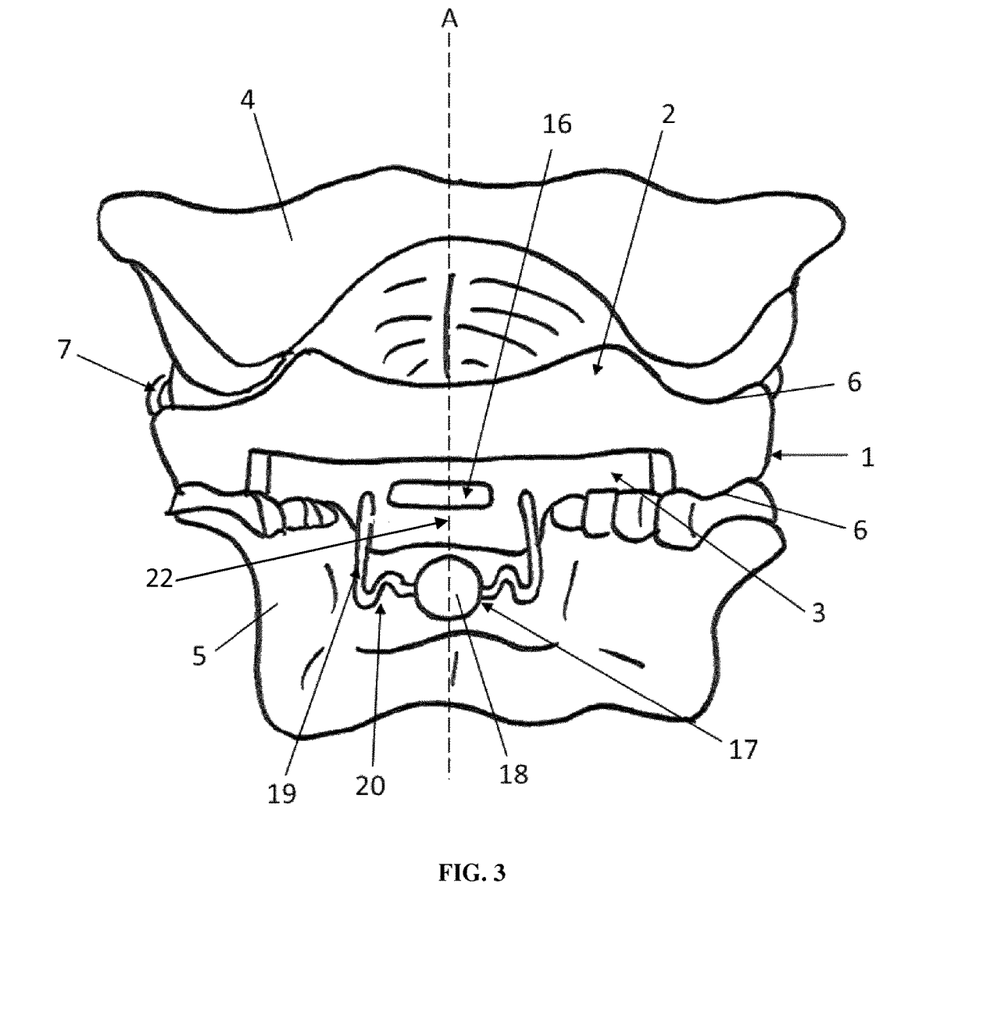
FIG. 3 is a drawing representing a perspective view of the interior of a user's mouth bearing the device according to the invention.

FIG. 3 shows a perspective view of the interior of a mouth fitted with the device according to the invention.

In one embodiment, the device (1) of the invention comprises a target (18). In one embodiment, said target is acting as a stimulating means (17).

In one embodiment, the target (18) is centered, in a transverse plane, with respect to the inferior dental arch. In one embodiment, the target (18) is centered, in a transverse plane, with respect to the cooperating means (2, 3), and preferably with respect to the lower cooperating means (3).

In one embodiment, the target (18) is located behind the inferior incisors. In one embodiment, the part of the target which is the closest to the inferior incisors is from 0.1 to 50 millimeters behind the front end (21) of the device (1), or from 0.1 to 40 millimeters behind the front end (21) of the device (1), or from 0.1 to 30 millimeters behind the front end (21) of the device (1), or from 0.2 to 25 millimeters behind the front end (21) of the device (1), or from 0.3 to 20 millimeters behind the front end (21) of the device (1), or preferably from 0.4 to 15 millimeters behind the front end (21) of the device (1), or more preferably from 0.5 to 10 millimeters behind the front end (21) of the device (1), or even more preferably from 0.5 to 5 millimeters behind the front end (21) of the device (1).

In one embodiment, the target (18) is located close to the lower cooperating means (3). In one embodiment, the target (18) is located close to the lower incisors.

In one embodiment, the target (18) is never located ahead of the incisors of the lower dental arch.

In one embodiment, the target (18) is not located at the level of the gap between the lower and upper incisors.

In one embodiment, the target (18) is located inside the oral cavity. In one embodiment, the target (18) is located in the inferior extension of the internal slope (22) of the lower cooperating means (3). In one embodiment, the target (18) is located in the inferior extension of the lower cooperating means (3) in order to exert pressure on the mucous zone covering the mental spines of the lower jaw (5). In one embodiment, the target (18) faces the tip of the tongue.

In one embodiment, the target (18) is a stimulating means (17) ensuring simultaneously protraction of the tongue and of the mandible. In one embodiment, the stimulating means (17) ensures efficient airways opening. In one embodiment, the target (18) has the same function as the stimulating means (17). In one embodiment, the device (1) induces a forward movement of the tongue.

In one embodiment, the device (1) of the invention comprises a stimulating means (17) for stimulation of the tongue muscles, preferably the genioglossus. The stimulating means (17) induces reflex exploration of said stimulating means (17) by the tongue, preferably the tip of the tongue. The exploring movements of the tongue, and especially advancement of the tongue, induce stimulation of the tongue muscles, preferably of the genioglossus.

In one embodiment, the device (1) of the invention comprises stimulating means (17) for stimulation of the genioglossus involving reflex exploration of said stimulating means (17) by the tongue, said stimulating means (17) being located on the cooperating means (2, 3), preferably the lower cooperating means (3). Preferably, said stimulating means (17) are located on the device such as when the device is inserted in the mouth, the stimulating means (17) is located at the rear of the lower incisors. Preferably, said stimulating means (17) being located on the device such as when the device is inserted in the mouth, the stimulating means (17) is located opposite to the mucous zone the mental spines.

Stimulating means (17) further present the advantage to be able to exert a pressure on the mucous zone covering the mental spines of the user inducing a reflex movement of the lower jaw (5). In one embodiment, said stimulating means (17) induces reflex mandibular advancement.

In one embodiment, said mandibular advancement represents from 30% to 70% of the maximum mandibular propulsion, preferably about 50% of the maximum mandibular propulsion.

In one embodiment, the device (1) ensures efficient opening of the upper airways by mandibular advancement coupled to lingual simulation.

According to one embodiment, stimulating means (17) comprise a target (18) able to move and preferably to rotate on itself.

According to an embodiment, the target (18) is made of a biocompatible, a non-allergenic substance, such as resin, for example acrylic resin or acetal resin, polymer or any polymer-based material know by one skilled in the art. According to another embodiment, any type of substance is conceivable for producing the target (18) according to the invention, such as for instance a composite. According to one embodiment, target (18) is made of flexible resin.

According to one embodiment, the target (18) is spherical. In a preferred embodiment, the target (18) is spherical and is able to rotate on itself around an axis passing by his center.

According to one embodiment, the target (18) is spherical, spheroidal or ellipsoidal.

According to one embodiment, the target (18) is able to rotate around at least one axis. According to one embodiment, the target (18) is able to rotate around one axis, or around two axes or around three axes.

According to one embodiment, the target (18) has at least five degrees of freedom, at least four degrees of freedom, at least three degrees of freedom, at least two degrees of freedom or at least one degree of freedom.

According to one embodiment, the target (18) is spheroidal, preferably is a prolate spheroid or an oblate spheroid. In a preferred embodiment, the target (18) is spheroidal and is able to rotate on itself around its axis of revolution.

According to one embodiment, the target (18) is ellipsoidal. In a preferred embodiment, the target (18) is ellipsoidal and is able to rotate on itself around one of its axis of revolution.

In one embodiment, the target (18) comprises a hole passing from side to side and located along a revolution axis.

According to an embodiment, the target (18) is advantageously placed opposite the mucous zone covering the mental spines.

In a preferred embodiment, the target (18) is carrier by bracket (19). Preferably, the bracket (19) passes inside the target (18), more preferably the bracket (19) passes inside the target (18) through a hole passing from side to side of the target and located along a revolution axis.

According to one embodiment (19), the bracket is made of a metal or a metal alloy.

In one embodiment, the target (18) comprises a tube, made from a metal or a metal alloy, through which pass the bracket (19), made from a metal or a metal alloy. Said tube defines the axis of revolution of the target (18).

In one embodiment, the target (18) comprises a tube or a cylinder made of a metal or a metal alloy allowing the passage of the bracket (19). In said embodiment, the bracket (19) passes inside the target (18) through said tube. As the bracket (19) is made of a metal or a metal alloy, the friction is reduced and the movement, preferably the rotation, facilitated between the bracket (19) and the target (18), due to a lower metal/metal friction coefficient instead of a polymer/metal coefficient. Thus the attractiveness of the target for the apex of the tongue and the stimulation of the tongue muscles especially the protractor muscles is enhanced. According to one embodiment, the tube is centered along one axis of revolution of the target (18).

According to one embodiment, the bracket (19) has an overall U-shape, the extremities of the two arms of the U being embedded in the cooperating means (2, 3), preferably in the lower cooperating means (3).

According to one embodiment, the bracket (19) has an overall U-shape, the extremities of the two arms of the U being embedded in the cooperating means (2, 3), preferably in the upper cooperating means (2).

According to one embodiment, the bracket (19) is located in the front part of the cooperating means (3), when considering that the cooperating means (3) has a general shape of a horseshoe and that the rear part corresponds to the both extremities of the horseshoe and the front part correspond to the rounded portion of the horseshoe.

According to one embodiment, the target (18), is on located the lower part of the U of the bracket (19).

According to an embodiment, the bracket (19) is advantageously produced from a steel wire presently used in the field of the invention.

According to one embodiment, the bracket (19) comprises centering means (20) for centering the target (18) relative to the device (1). The target (18) is preferably centered relative to plane A as represented in FIG. 3. Plane A is the vertical plane of symmetry of the user's head.

Centering of the target is necessary to avoid that the tongue muscles works non-symmetrically whereas the tongue is a pair muscle.

According to one embodiment, centering means (20) are for example two S-shapes symmetrically made on the bracket (19). As shown in FIG. 3, the target (18) can move only slightly laterally on the bracket (19) due to the presence of the two S-shapes of the centering means and therefore remains centered in the user's mouth. Centering means (20) shall not prevent the target (18) to rotate on itself.

In another embodiment, the bracket (19) does not comprise centering means (20).

In one embodiment, the target (18) is not a tongue rest. In one embodiment, the target (18) is not a tongue lowering device. In one embodiment, the main object of the target (18) is not to prevent the tongue from flapping backward. In one embodiment, the target (18) is not adapted to lay upon the tongue of the patient to prevent the tongue from falling across and blocking the patient's airway.

In one embodiment, the device of the invention (1) does not give a burden on muscles of the tongue. In one embodiment, the target (18) or the stimulating means (17) of the invention does not give a burden on muscles of the tongue.

In one embodiment, the device (1) of the invention comprises stimulating means (17), which attract the apex—or tip—of the tongue.

In one embodiment, the target (18) is not removable. In one embodiment, the bracket (19) is not detachably connected to the lower cooperating means (3).

In one embodiment, the target (18) does not comprise a flat part or a flat tongue component such that the tongue cannot lie flat on the target. In one embodiment, the target (18) is designed to attract the apex or the tip of the tongue and not to allow the flat portion of the tongue to rest.

In one embodiment, the target (18) has not a triangular form.

In one embodiment, the bracket (19) has an overall U-shape and not an overall stirrup-shape.

In one embodiment, the device of the present invention does not comprise a palate contact or a palate connection.

In one embodiment, the device of the present invention does not comprise a spring.

FIGS. 4, 5 and 6 show a perspective front view and side view and a third perspective view, respectively, of the device according to the invention fixed on the upper jaw (4).

It will be seen from FIGS. 4, 5 and 6 that the stimulating means (17) are located in the very lower part of the device of the invention.

It is common knowledge for one person skilled in the art to modify the length of the arms of the U-shaped bracket (19) so that the target (18) is located opposite to the mental spine of the user.

According to one embodiment, stimulating means (17) are also means for delivering an active agent, preferably a therapeutic agent selected from the group comprising hypnotic agents, myo-relaxing agents, anti-apnea agents or a mixture thereof.

In one embodiment, the stimulating means (17) comprises an active agent. In one embodiment, the active agent is present at the surface of the target (18). In another embodiment, the active agent is present into the target (18). In another embodiment, the active agent is present at the surface and into the target (18). When the active agent is present into the target (18), the target (18) may be made of a porous material so that the active agent may be released in the mouth.

In another embodiment, the target (18) is made of an edible erodible material comprising an active agent. Action of the tongue on target (18) may for example dissolves the active agent in salivary.

The device of the present invention may be used to treat and/or prevent and/or correct obstructive sleep apnea syndrome in adults or in children. Especially for children, device of the present invention may further comprise characteristic elements of a pacifier.

In this specific embodiment, the device (1) of the invention further comprises a stop disc and optionally a grip.

In one embodiment, the device (1) and the grip are fixed on either side of the stop disc.

When the device of the invention comprises elements of a pacifier, fixing means (7) are not present on the cooperating means (2). This is especially preferred for children without teeth. In this case, cooperating means (2) and (3) are preferably smooth.

In one embodiment, the device of the invention comprises a chip cookie. The presence of such a chip cookie may enable to follow the compliance of the treatment by the patient.

The device of the present invention induces tongue advancement by reflex exploration of the target (18) by the tongue. According to the Applicant's understanding, the fact the target (18) is able to rotate on itself is particularly attractive for the tongue and therefore induces repeated explorations. Without willing to be bound by a theory, it is hypothesized by the Applicant that during sleep, the tongue regularly moves into the mouth and meet the target (18). While exploring the target (18), the tongue makes it rotate on itself, which reinforce the attractiveness of this foreign body and prolong the exploration. The stimulation of the genioglossus and the subsequent opening of the upper airways by this induced tongue displacement last therefore longer.

Therefore, the device of the invention opens the airway of a sleeping individual who suffers from snoring, obstructive sleep apnea syndrome and/or other airway disorders.

The device of the present invention further presents the advantage of being able to exert a pressure on the mucous zone covering the mental spines of the lower jaw. Especially the target (18) or the stimulating means (17) are also able to exert a pressure on the mucous zone covering the mental spines of the lower jaw. The stimulation deriving from the pressure exerted on the mucous zone covering the mental spines is transmitted to the central nervous system, which transforms it into efferent motor messages. Mandibular advancement of the lower jaw (5) is stimulated and induced in this way. Given the reception of the efferent motor messages deriving from the stimulation of the mucous zone covering the mental spines, no viscoelastic muscle reaction is generated, and the mandibular advancement is induced by a reflex reaction, not forced. In one embodiment, the device of the invention (1) ensures mandibular advancement coupled to functional reeducation, especially reeducation of the tongue. In on embodiment, the device of the invention (1) ensures mandibular advancement through proprioceptive mechanism. In said embodiment, sensitive stimulation leads to motor effect.

According to the Applicant, the device of the invention presents the following advantages: the cooperating means (2, 3) are in the form of a tray which comprises fixing means (7) for fixing the device on the upper jaw (4) and which can cooperate with the lower jaw (5). Said fixing means is at least one ball end clasp, preferably two ball end clasp on each side. The cooperating means (2, 3), preferably the lower cooperating means (3), further comprises a notch at its forward end to induce without any external constraint the advanced forward position of the lower jaw (5). Said notch maintains the lower jaw (5) in a forward position without blocking the backwards mobility of the lower jaw (5). The device also further comprises a target (18) which is able to exert a pressure on the mucous zone covering the mental spines of the lower jaw when the lower jaw (5) returns to a rear position. Then the lower jaw returns back naturally to its forward position (due to an avoidance reflex) and cooperates again with the notch, thereby maintaining a forward position that is not forced. In addition, in the same time, said target attracts the tongue and mobilizes the protractor muscles of the tongue, thereby facilitating the reflex mandibular advancement.

The device (1) according to the invention is adapted for the treatment, prevention and/or correction of obstructive sleep apnea syndrome, snoring and/or other airway disorders such as breathing through the mouth or obstructive airway disorders.

In one embodiment, patients are adults. In another embodiment, patients are children.

The present invention further relates to a method for treating, preventing and/or correcting a patient having obstructive sleep apnea syndrome, snoring and/or breathing through the mouth, the method comprising: inserting into a patient's mouth the device of the invention.

The present invention further relates to a method for reeducating a patient having obstructive sleep apnea syndrome, snoring and/or breathing through the mouth, the method comprising: inserting into a patient's mouth the device of the invention.

The present invention further relates to a method to muscle the genioglossus, the method comprising: inserting into a patient's mouth the device of the invention.

The present invention further relates to a method for reprogramming the muscles of the tongue, especially the genioglossus, in order to cause a decrease resistance to airflow in the pharynx, the method comprising: inserting into a patient's mouth the device of the invention.

The present invention also relates to the use of the device for treating, preventing and/or correcting obstructive sleep apnea syndrome, snoring and/or other sleeping airway disorders in a subject in need thereof, said subject being an adult or a child.

The invention also relates to a method of designing the device of the invention (1), the method comprising designing the device of the invention according to the patient's morphology by computer-aided design (CAD).

According to one embodiment, the device (1) of the invention is customized and adapted of each patient.

The invention also relates to a method of manufacturing the device of the invention (1), the method comprising producing the device of the invention by computer-aided manufacturing (CAM).

The invention further relates to a method of manufacturing the device of the invention, the method comprising producing the device of the invention, measuring a portion of a patient's oral cavity; and sizing the tray (6) to fit the measured oral cavity.

The invention also relates to a kit of parts comprising on one hand the upper and lower cooperating means (2) and (3) and on the other hand the target (18) and the bracket (19).

The manufacture of the device of the invention may be performed by methods known by the skilled artisan.

In one embodiment, the device of the invention is customized to fit the patient's oral cavity. In another embodiment, the device of the invention is not particularly customized to fit the patient's oral cavity.

The invention claimed is:

1. An intraoral device to be inserted in the mouth of an animal or a human, comprising:
   an upper cooperating element adapted to cooperate with the upper jaw;
   a lower cooperating element adapted to cooperate with the lower jaw;
   a bracket fixed in the cooperating means; and
   a target carried by the bracket;
   wherein the upper and lower cooperating elements are connected and
   wherein:
   said bracket has an overall U-shape;
   said target is spherical such that the center of the target is configured to be centered longitudinally in a central part of the bracket and the target is configured to be located in the lingual area of the lower incisor mucosa,
   said target has at least one degree of freedom relative to the bracket,
   said target is a stimulating element inducing reflex mandibular advancement, said mandibular advancement being held by muscles, and
   said target attracting a tongue inducing mobilization of protractor muscles of the tongue.

2. The intraoral device according to claim 1, wherein said target
   is located from 0.1 to 30 millimeters behind a front end of the device;
   is located in the inferior extension of the lower cooperating element; and
   is centered, in a transverse plane, with regard to the upper and lower cooperating elements.

3. The intraoral device according to claim 2, wherein said stimulating element stimulates protractor tongue muscles, or genioglossus, and involves reflex exploration by a tongue of said stimulating element.

4. The intraoral device according to claim 1, wherein said upper and lower cooperating elements are fixed one relative to the other.

5. The intraoral device according to claim 1, wherein said upper cooperating element comprises a fixing element to the upper jaw; said fixing element comprising at least one clasp, or an Adam's clasp or a ball end clasp.

6. The intraoral device according to claim 1, wherein extremities of two arms of the U-shaped bracket are embedded in the cooperating elements.

7. The intraoral device according to claim 1, wherein said bracket comprises an obstacle on each side of the target, in such a way that said target remains centered in the bracket.

8. The intraoral device according to claim 1, wherein said target, said upper cooperating element and/or said element cooperating means are made of a biocompatible, non-allergenic substance, or a polymer or a resin.

9. The intraoral device according to claim 1, wherein said target is able to rotate around at least one axis.

10. The intraoral device according to claim 1, wherein said target comprises a metallic tube through which the bracket passes.

11. The intraoral device according to claim 1, wherein said target comprises an active agent.

12. A method for treating, preventing and/or correcting obstructive sleep apnea syndrome, snoring and/or other airway disorders comprising insertion in the mouth of a subject in need thereof of an intraoral device;
   said mouth having an upper and a lower jaw, said device comprising:
   an upper cooperating element adapted to cooperate with the upper jaw;
   a lower cooperating element adapted to cooperate with the lower jaw;
   a bracket fixed in the cooperating elements; and
   a target carried by the bracket;
   wherein the upper and lower cooperating elements are connected and
   wherein:
   said bracket has an overall U-shape;
   said target is spherical such that the center of the target is configured to be centered longitudinally in a central part of the bracket and the target is configured to be located in the lingual area of the lower incisor mucosa,
   said target has at least one degree of freedom relative to the bracket, and
   said target is a stimulating element inducing reflex mandibular advancement, said mandibular advancement being held by muscles, and attracting a tongue inducing mobilization of protractor muscles of the tongue.

13. The method according to claim 12, wherein said subject is a child.

14. An intraoral device to be inserted in the mouth of an animal or a human, comprising:
   an upper cooperator adapted to cooperate with an upper jaw, the upper cooperator being a first tray adapted to fit the teeth;
   a lower cooperator adapted to cooperate with a lower jaw, the lower cooperator being connected to the upper cooperator, the lower cooperator being a second tray or a ramp adapted to fit the teeth;
   a bracket fixed in the cooperators; and
   a target carried by the bracket;
   wherein:
   said bracket has an overall U-shape;
   said target is spherical such that the center of the target is configured to be centered longitudinally in a central part of the bracket and the target is configured to be located in the lingual area of the lower incisor mucosa,
—said target has at least one degree of freedom relative to the bracket, and said target is a stimulating element inducing reflex mandibular advancement, said mandibular advancement being held by muscles, and attracting a tongue inducing mobilization of protractor muscles of the tongue.

15. The intraoral device according to claim 14, wherein said target is located from 0.1 to 30 millimeters behind a front end of the device;

is located in the inferior extension of the lower cooperator; and is centered, in a transverse plane, with regard to the upper and lower cooperators.

16. The intraoral device according to claim 14, wherein said stimulator stimulates protractor tongue muscles, or the genioglossus, and involves reflex exploration by a tongue of said stimulator.

17. The intraoral device according to claim 14, wherein said upper and lower cooperators are fixed one relative to the other.

18. The intraoral device according to claim 14, wherein said upper cooperator fixes to the upper jaw by at least one clasp, or an Adam's clasp or a ball end clasp.

* * * * *